US012740768B2

(12) United States Patent
Peng et al.

(10) Patent No.: US 12,740,768 B2
(45) Date of Patent: Sep. 22, 2026

(54) METHOD FOR ULTRASONIC PANORAMIC IMAGING

(71) Applicant: Medlander Medical Technology Inc., Nanjing (CN)

(72) Inventors: Kun Peng, Nanjing (CN); Feng Yin, Nanjing (CN)

(73) Assignee: Medlander Medical Technology Inc., Nanjing (CN)

(*) Notice: Subject to any disclaimer, the term of this patent is extended or adjusted under 35 U.S.C. 154(b) by 133 days.

(21) Appl. No.: 18/837,369

(22) PCT Filed: Oct. 24, 2022

(86) PCT No.: PCT/CN2022/127079
§ 371 (c)(1),
(2) Date: Aug. 9, 2024

(87) PCT Pub. No.: WO2023/206994
PCT Pub. Date: Nov. 2, 2023

(65) Prior Publication Data

US 2025/0169799 A1 May 29, 2025

(30) Foreign Application Priority Data

Apr. 24, 2022 (CN) ........................ 202210433988.5

(51) Int. Cl.

| | |
|---|---|
| ***A61B 8/00*** | (2006.01) |
| ***G06T 3/4038*** | (2024.01) |
| ***G06T 7/33*** | (2017.01) |

(52) U.S. Cl.
CPC .......... *A61B 8/5253* (2013.01); *G06T 3/4038* (2013.01); *G06T 7/337* (2017.01);
(Continued)

(58) Field of Classification Search
CPC ....... A61B 8/5253; A61B 8/523; A61B 8/463; A61B 8/483; A61B 8/5207; A61B 8/0891;
(Continued)

(56) References Cited

U.S. PATENT DOCUMENTS 9,563,965 B2 * 2/2017 Kume ..................... G06T 7/215
12,541,893 B2 * 2/2026 Chen ...................... A61B 8/145
(Continued)

FOREIGN PATENT DOCUMENTS

CN 1839760 A 10/2006
CN 101901481 A 12/2010
(Continued)

OTHER PUBLICATIONS

"Image stitching algorithm research based on OpenCV"; Kaili Chen, Proceedings of the 33rd Chinese Control Conference (2014, pp. 7292-7297) (Year: 2014).*
(Continued)

*Primary Examiner* — Michael S Osinski
(74) *Attorney, Agent, or Firm* — Potomac Law Group, PLLC

(57) ABSTRACT

The present application discloses a method for ultrasonic panoramic imaging. Through processes such as coordinate mapping calculation, interpolation, and secondary correction of two images, the to-be-stitched image becomes more accurate, and it is also possible to avoid problems that may arise from noise, tissue movement leading to abnormal images. Furthermore, after a first stitching is completed, the to-be-stitched image is saved as a reference image for use in a next registration. Due to the improved accuracy of the reference image, the continuity and accuracy of subsequent panoramic imaging processes can be ensured.

10 Claims, 7 Drawing Sheets

(52) U.S. Cl.
CPC ............... *G06T 2207/10132* (2013.01); *G06T 2207/20021* (2013.01); *G06T 2207/20212* (2013.01)

(58) Field of Classification Search
CPC ..... A61B 8/488; A61B 8/5246; A61B 8/4245; A61B 8/469; A61B 8/5238; G06T 3/4038; G06T 7/337; G06T 2207/10132; G06T 2207/20021; G06T 2207/20212; G06T 2207/20221; G06T 7/30
See application file for complete search history.

(56) References Cited

U.S. PATENT DOCUMENTS

2003/0036701 A1 2/2003 Dong et al.
2005/0089244 A1* 4/2005 Jin ........................ G06T 3/4038 382/284
2007/0073145 A1* 3/2007 Fan ........................ A61B 8/463 600/437
2012/0316441 A1* 12/2012 Toma ..................... A61B 8/483 600/443
2013/0022252 A1* 1/2013 Chen ..................... G06T 3/4038 382/131
2014/0031687 A1* 1/2014 Kurita ...................... A61B 8/54 600/440
2014/0063182 A1* 3/2014 Shin ..................... A61B 8/5276 348/36
2015/0348250 A1* 12/2015 Nakai ...................... G09G 3/20 345/635
2016/0335742 A1* 11/2016 Yim ...................... G06T 3/4038
2017/0116768 A1 4/2017 Yen et al.
2017/0200261 A1* 7/2017 Choi .................... A61B 8/5207
2019/0073779 A1* 3/2019 Iwase ..................... A61B 3/102
2019/0318178 A1* 10/2019 Kauffmann ............... G06T 7/55
2019/0328361 A1* 10/2019 Halmann .............. G06T 3/4038
2020/0037995 A1* 2/2020 Chen .................... A61B 8/0891
2020/0175663 A1* 6/2020 Horita ................... G06T 7/0002
2020/0193608 A1* 6/2020 Sato ....................... G06V 20/46
2020/0302595 A1* 9/2020 Iwabuchi .............. G06T 3/4038
2020/0411165 A1* 12/2020 Torii ...................... G16H 30/20
2021/0012490 A1* 1/2021 Sabczynski ........... G06T 7/0012
2021/0349211 A1* 11/2021 Halmann ................. A61B 8/54
2023/0281839 A1* 9/2023 Ng ....................... G06V 10/245 382/173
2023/0414201 A1* 12/2023 Mine ...................... A61B 8/466
2024/0180528 A1* 6/2024 Aono ....................... A61B 8/54

FOREIGN PATENT DOCUMENTS

CN 102274042 A 12/2011
CN 106815808 A 6/2017
CN 109636714 A 4/2019
CN 114848001 A 8/2022
RU 2626551 C1 7/2017

OTHER PUBLICATIONS

International Search Report and Written Opinion for International Application No. PCT/CN2022/127079 dated Nov. 2, 2023.

* cited by examiner

Graph for Elements Corresponding to arrLUT Data

METHOD FOR ULTRASONIC PANORAMIC IMAGING

CROSS-REFERENCE TO RELATED APPLICATIONS

The present application is a U.S. national stage filing under 35 U.S.C. § 371 of International Application No. PCT/CN2022/127079 filed on Oct. 24, 2022, which claims priority to Chinese patent application No. 202210433988.5, filed on Apr. 24, 2022, both of which are incorporated herein by reference in their entireties.

TECHNICAL FIELD

The present application relates to a field of ultrasonic image computer processing technology.

BACKGROUND

Panoramic imaging refers to stitching of a series of two-dimensional images acquired by moving a probe in a same plane into a continuous image. Due to a large amount of data processing required, this technology typically utilizes high-speed processors or computers to reconstruct the single image and is increasingly widely used in the field of data acquisition for large objects using a small probe, such as collection of fingerprints using miniature probes. Particularly, in the field of medical ultrasonic imaging, for a purpose of assisting medical diagnosis, higher requirements and widespread demand exist for this technology.

Taking ultrasonic instruments as one example, due to non-invasiveness, convenience, and reliability of ultrasound, ultrasonography has become a common auxiliary means for doctors to observe internal body parts and diagnose illnesses. Doctors can obtain ultrasonic images corresponding to internal parts by operating a probe placed on the surface of the skin. However, the area scanned by the probe is typically limited, thus restricting the size of a single-frame ultrasonic image that the doctor can see. When a single frame cannot display the entire panorama of a part, the doctors have no choice but to move the probe back and forth to observe different areas of this part. Accordingly, when the area to be measured cannot fit within a single image, it is not possible to directly measure the size of the area using measurement function common to most ultrasonic devices. With the panoramic imaging technology, a series of images generated from the doctor's back-and-forth scanning in the same plane can be stitched together into one extended ultrasonic image Based on correlation between the images, making it also convenient for measuring a large object area.

Panoramic imaging basically includes two steps of registration and stitching. The registration process takes advantage of a feature of a maximum correlation between adjacent frames to search for one and the same target area in a reference image and calculate the overall displacement trend of a current frame based on a movement trajectory of the target area. Registration is a very important step in the process of ultrasonic panoramic imaging, and two frames involved in the registration must have sufficient similarity to obtain highly accurate registration coefficients. It is generally believed that a key step in obtaining a correct panoramic image lies in the registration.

In the case of image registration, U.S. Pat. Nos. 5,566,674 and 6,605,042B2 both utilize a method of calculating transformation coefficients between two images through the application of SAD (Sum of Absolute Differences) and MLS (Minimum Least Squares), with general steps as follows:

1. Segmenting image(s) into several areas
2. Using the SAD method to find local motion vectors
3. Correcting the local motion vectors with fuzzy logic
4. Calculating and obtaining, through the algorithm of minimum least squares MLS from the local vectors, the final transformation coefficients (offx, offy, θ), i.e., displacement in the x-direction, displacement in the y-direction, and rotation angle respectively;
5. Stitching the image according to the transformation coefficients into the panoramic image.

The above method is disadvantageous in following aspects. The data of each point within the areas segmented from the image are directly used to calculate the offset by Sum of Absolute Differences (SAD), which will reduce accuracy of calculation results if the image contains large areas with insignificant gradient changes. Also, the method of calculating the rotation angle between images with Sum of Absolute Differences (SAD) requires a range of rotation and a step interval of each rotation angle to be primarily determined, but the step interval of the angle is difficult to be determined. Using a stitched image for registration, theoretically the two images with the highest correlation should be the consecutive ones. Since the stitched image are subjected to a certain processing and calculations, the accuracy of registration using a stitched image will be lower than that of directly comparing the two consecutive images for registration.

Experiments have proven that due to factors such as ultrasonic image noise and tissue motion, the transformation coefficients obtained through SAD and MLS may be inaccurate, leading to significant abnormalities in the final stitched panoramic image.

Chinese Patent CN1839760A also discloses a method for image registration as follows:

1. Segmenting image(s) into several areas
2. Obtaining a motion vector of a current frame relative to a registration image
3. Judging whether the obtained motion vector falls within a control range; if not, adjusting image extraction interval and repeating the step.
4. Fitting local motion vectors into final transformation coefficients This method, although enhancing the reliability of imaging by judging whether the motion vectors fall within a reasonable range after the SAD is performed, still fails to avoid the problem of insufficient precision in the transformation coefficients under the influence of noise and tissue motion. For the final stitching procedure, a comprehensive transformation coefficient (offx, offy, θ) is employed to determine a geometric relationship between the stitched image and the registered image, lacking precise capture of local variations between the two images, thereby compromising the continuity manifested in the stitched image.

SUMMARY

In view of the shortcomings in the prior art as described above, the technical problem to be solved by the present application is to propose a method for ultrasonic panoramic imaging capable of stitching a series of local images into a panoramic image with high speed and great accuracy, so as to meet the extremely high requirements of ultrasonic equipment for medical diagnosis.

To solve the above problems, the method for ultrasonic panoramic imaging according to the present application may utilize the following technical solution.

A method for ultrasonic panoramic imaging, comprises steps of:

(1) Acquiring one frame from to-be-stitched images, determining whether this frame is a first frame among a plurality of to-be-stitched images, and directly using it as an initial reference image C if it is the first frame or otherwise proceeding to step (2) if it is not the first frame;

(2) Acquiring an image A other than the reference image C, expanding a perimeter of the image A based on values of neighboring pixels thereof to generate image A*, and expanding a perimeter of the reference image C based on values of neighboring pixels thereof to generate an image C*;

(3) Dividing the image A* and the image C* equally into n areas, calculating by SAD method average offset of image A* relative to the image C* in each area, where n is a positive integer;

(4) Obtaining average offset values in X and Y directions of image coordinates in image A* relative to the image C* for each of the n areas, adding corresponding average offsets to the coordinates of the center points of each area respectively to acquire a new coordinate of n points for the image A relative to the image C, obtaining average offsets of the overall image by averaging the new coordinates of the n points, and obtaining coordinate mapping values for all points of image A relative to the image C after interpolation is performed on the new coordinates of the n points;

(5) Traversing each pixel of the image A based on the obtained coordinate mapping values, performing a mapping thereon according to corresponding coordinates and deforming it into registered image B;

(6) Traversing each pixel of the registered image B and the reference image C, calculating a difference of pixels at corresponding positions to obtain a set of pixel differences; traversing the set of pixel differences, comparing with 99 respectively and taking the smaller value to obtain a new set of difference;

(7) Obtaining a lookup table based on a calibration curve;

(8) Correcting the registered image B to obtain a to-be-stitched image B*; and (9) Stitching, by weighted average method for overlapping areas, the to-be-stitched image B* with one previous panoramic resulting image C based on overall average offset, to obtain a composite image D.

Compared to the prior art, the present application is advantageous in the following aspects. Since only the offset of the new image is calculated in the prior art through SAD and MLS, inaccuracies in calculation can result from factors such as noise and tissue motion, leading to significant anomalies in panoramic images. By contrast, in the present application, through processes such as coordinate mapping calculation, interpolation, and secondary correction for the two images, greater precision in the to-be-stitched image is achieved, thereby avoiding potential issues caused by the noise and the tissue motion that could lead to image anomalies. Furthermore, upon the completion of primary stitching, the to-be-stitched image is saved as the reference image for subsequent registration. The accuracy of the reference image is enhanced, thereby ensuring the continuity and precision of images in subsequent panoramic processes.

The present application further provides a computer device, comprising a memory, a processor, and a computer program stored on the memory and executable on the processor, wherein the steps of the above method are implemented when the computer program is executed by the processor.

The present application further provides a computer-readable storage medium having a computer program stored thereon, wherein the steps of the above method are implemented when the computer program is executed by a processor.

DETAILED DESCRIPTION

The present application will be described below in further details with reference to the accompanying drawings and embodiments.

Figure 1:
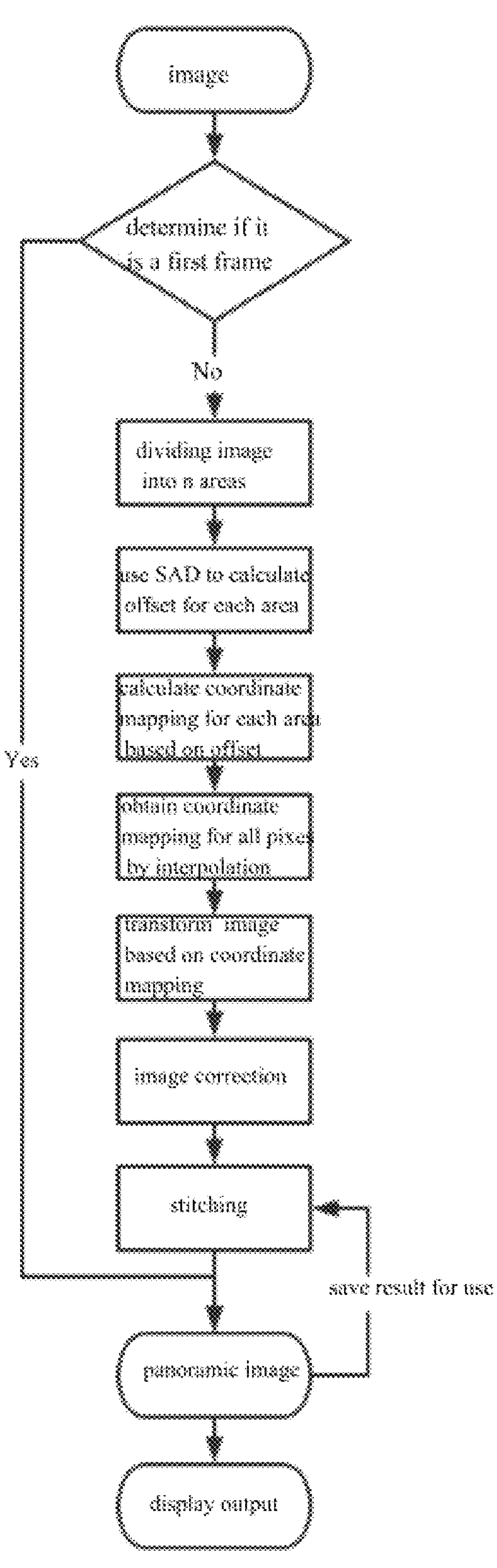
FIG. 1 illustrates a flowchart of a method for ultrasonic panoramic imaging according to the present application.

As shown in FIG. 1, the present application provides a method for ultrasonic panoramic imaging, comprising the following steps:

(1) Acquiring one frame from to-be-stitched images, determining whether this frame is a first frame among a plurality of to-be-stitched images, and directly using it as an initial reference image C if it is the first frame or otherwise proceeding to step (2) if it is not the first frame.

(2) Acquiring an image A other than the reference image C, expanding a perimeter of the image A based on values of neighboring pixels thereof to generate image A*, and expanding a perimeter of the reference image C based on values of neighboring pixels thereof to generate an image C*.

Figure 2:
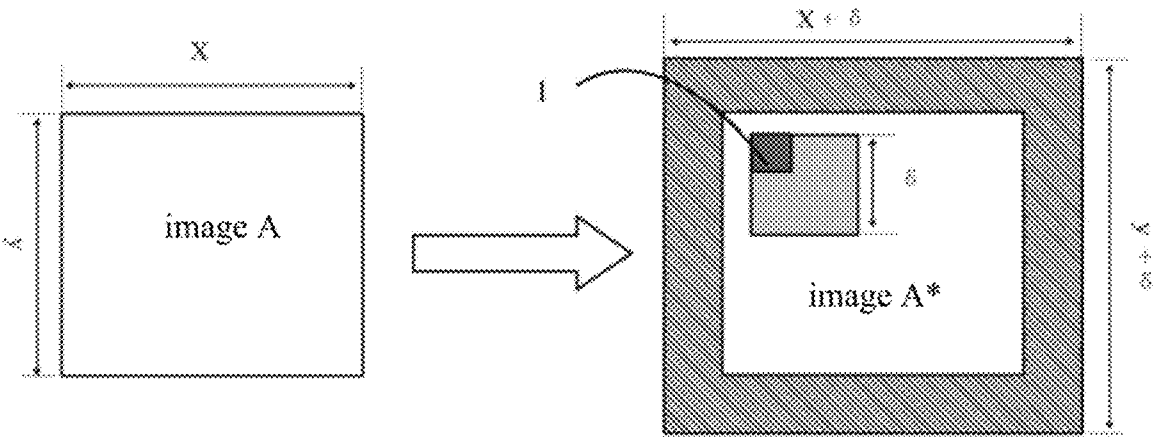
FIG. 2 illustrates a schematic diagram showing expansion of Image A by surrounding pixel values to Image A* in step (2).

As illustrated in FIG. 2, assume that the basis for expansion is a square-shaped region with a side length of 6, while image A has a length of x and a width of y. Consequently, the expanded image becomes a rectangle with a length of $x+\delta$ and a width of $y+\delta$. The pixel values of the expanded portion are set as those of the nearest points within image A (for example: regarding the pixel value of the top-left corner point of image A*, its nearest point relative to image A is the top-left corner point of image A; therefore, its pixel value is set as the pixel value of the top-left corner point of image A). Through this process, a new image A* is obtained. The same applies to the reference image C, expanding by the area of a square-shaped region with a side length of δ, resulting in a new image C*.

The side length δ of the square-shaped region should have a minimum value no less than one-tenth of a shorter side of the original image, and a maximum value not exceeding one-third of the shorter side.

(3) Dividing image A* and the image C* equally into n areas, calculating by SAD method, average offset of image A* relative to the image C* in each area, where n is a positive integer.

Figure 3:
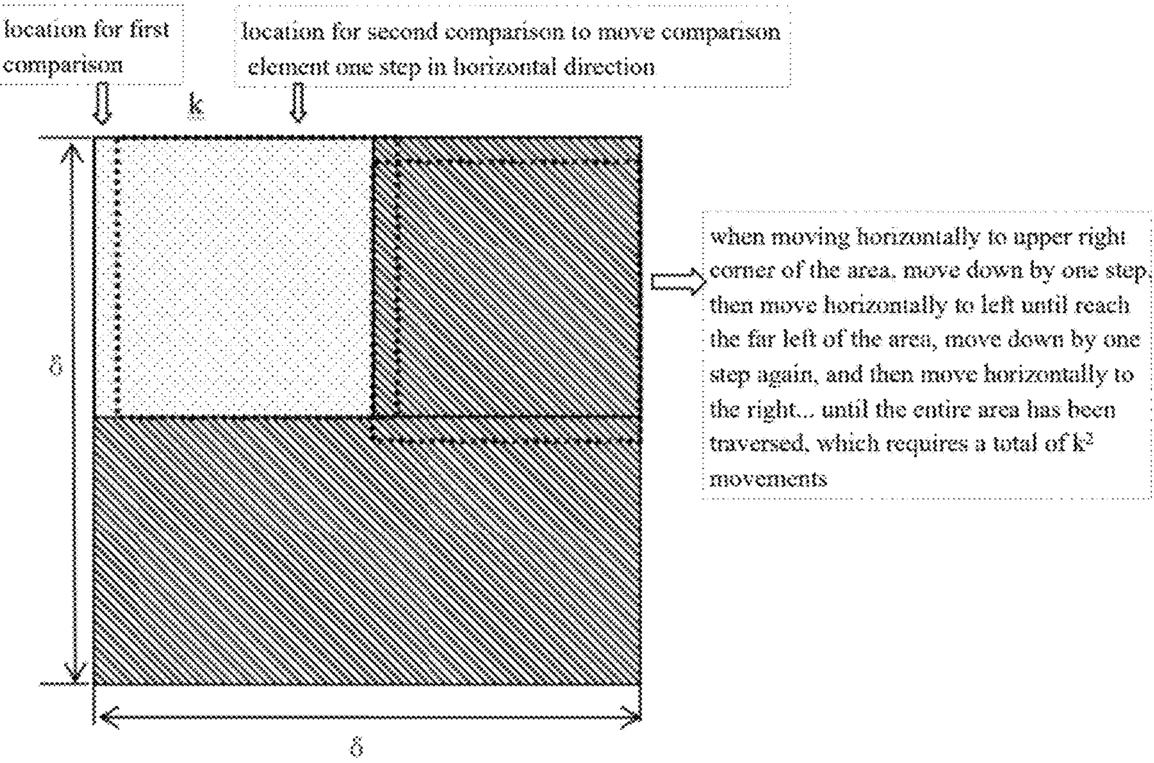
FIG. 3 illustrates a schematic diagram showing SAD (Sum of Absolute Differences) calculation performed by a comparison unit in step (3).

(3.1) Setting a square-shaped comparison unit 1 as a minimum comparison range for each area, and in a first comparison operation, the area where the comparison unit is located in upper left corner of $A^*_1$ is denoted as $Kernel_1$, and area where the comparison unit is located in upper left corner of $C^*_1$ is denoted as $Kernel_2$, as shown in FIG. 3;

(3.2) Performing subtraction on each pixel point of $Kernel_1$ and $Kernel_2$ to calculate the difference with the pixel values of corresponding points and obtain differences of a plurality of corresponding pixels, then summing up the differences of all the pixels to obtain the Sum of Absolute Differences (SAD) results for $Kernel_1$ and $Kernel_2$ denoted as $Sum_1$, and saving center coordinate common to $Kernel_1$ and $Kernel_2$ denoted as $(x_1, y_1)$;

(3.3) Moving, in a second comparison, $Kernel_1$ and $Kernel_2$ one step to right side respectively and continuing to repeat step (3.2) to obtain a second SAD result denoted as $Sum_2$ and coordinate $(x_2, y_2)$, repeating step (3.2) again to further move $Kernel_1$ and $Kernel_2$ one step to right side until $Kernel_1$ and $Kernel_2$ move to the upper right corner of $A^*_1$ and $C^*_1$, then moving one step downward to continue with the SAD calculation until $Kernel_1$ and $Kernel_2$ move across the entire areas of $A^*_1$ and $C^*_1$; obtaining $k^2$ SAD results including $k^2$ Sum values;

(3.4) Identifying a minimum value out of said $k^2$ Sum values and a coordinate value $(x_{min}, y_{min})$ corresponding to the minimum value to serve as a final calculation result for this area, and this coordinate value represents the coordinate of the position with the highest similarity in position within the area of the two images; and (3.5) Calculating the average offset value for this area in which coordinate of the center point of the area is subtracted from the coordinate value $(x_{min}, y_{min})$ to obtain the average offsets OffsetX1 and OffsetY1 in X and Y directions.

(4) Obtaining average offset values in X and Y directions of image coordinates in image A* relative to the image C* for each of the n areas, adding corresponding average offsets to the coordinates of the center points of each area respectively to acquire a new coordinate of n points for the image A relative to the image C, obtaining average offsets of the overall image by averaging the new coordinates of the n points, and obtaining coordinate mapping values for all points of image A relative to the image C after interpolation is performed on the new coordinates of the n points. Because the new coordinates of the n center points in image A relative to the image C are merely coordinate positions of a few points within the entire image, to obtain the coordinate mapping positions of all points within the image, an interpolation operation is required. Generally, linear interpolation, which is a relatively simple method and widely applied, suffices. Currently, numerous open-source APIs provide functions to implement the linear interpolation. In the present application, the interpolation API provided by OpenCL is utilized. After interpolating the newly mapping coordinates of the n points in the image A relative to the image C, the coordinate mapping values of all points in image A relative to the image C are obtained.

(5) Traversing each pixel of image A based on the obtained coordinate mapping values, performing a mapping thereon according to corresponding coordinates and deforming it into a registered image B. Specifically, the process of traversing each pixel of the image A, performing a mapping thereon according to corresponding coordinates and deforming it into the registered image B is performed with a formula given by dst[x,y]=src[yMap[x,y], xMap[x,y]], where dst denotes a target image, i.e., registered image B; src denotes a source image, i.e., image A; x and y represent x-axis coordinate and y-axis coordinate, respectively; and yMap and xMap represent y-coordinate mapping and x-coordinate mapping from coordinate mapping values of all points of image A relative to the image C in step (4).

(6) Traversing each pixel of the registered image B and the reference image C, calculating a difference of pixels at corresponding positions to obtain a set of pixel differences; traversing the set of pixel differences $\{Diff_{[0,0]}, Diff_{[0,1]} \ldots Diff_{[x,y]}\}$, comparing with 99 respectively and taking the smaller value to obtain a new set of difference $\{Diff^*_{[0,0]}, Diff^*_{[0,1]} \ldots Diff^*_{[x,y]}\}$.

(7) Obtaining a lookup table based on a calibration curve given by OutputValue=InitialValue+(FinalValue−InitialValue)/(1+exp(−Slope*4*(InputValue−Brkpt))), where InitialValue denotes an initial value of the curve; FinalValue denotes a final value of the curve; Slope is a slope of the curve; Brkpt denotes a value of inflection point of the curve; InputValue denotes input parameter, which is a collection consisting of a plurality of numerical values; and OutputValue denotes a set of output values obtained by substituting the values of "InputValue", which is referred to as the lookup table and is denoted as the arrLUT dataset.

(8) Obtaining a set of registration coefficient $Coeff_{x*y}$ in accordance with a formula given by Coeff[i]=arrLUT [Diff*[i]]i∈[0,x*y), and correcting the registered image B based on a formula given by ImageB[i]=Coeff[i] *ImageB[i]+(1−Coeff[i])*ImageC[i] where i∈[0, x*y), ImageB[i] denotes i-th pixel of image B, ImageC[i] denotes i-th pixel of image C, resulting in the to-be-stitched image B*.

(9) Stitching, by weighted average method for overlapping areas, the to-be-stitched image B* with one previous panoramic resulting image C based on overall average offset, to obtain a composite image D. Specifically, the process of the stitching by the weighted average method is specified by the following steps.

(9.1) Stitching the to-be-stitched image B* onto the reference image C based on the overall average offset OffsetX and OffsetY, to obtain the composite image D, wherein there is an overlapping area between the two images in the composite image D which requires further correction and smoothing.

(9.2) setting an overlap coefficient SpaceCoeffCount, indicating that image correction is performed for the area having a width SpaceCoeffCount in the overlapping area, and obtaining a correction dataset arrCoefficient with a number of SpaceCoeffCount in accordance with a formula given by arrCoefficient[i]=((i+1))/SpaceCoeffCount where i∈[0, SpaceCoeffCount).

(9.3) Basing on a formula given by ImageD[x,y]=(1−arrCoefficient[x])*ImageC[x,y]+arrCoefficient[x]*ImageB*[x,y], where [x,y] denotes coordinate of a point in the image, ImageD denotes the composite image D, ImageC denotes the reference image C, and ImageB* denotes the to-be-stitched image B*.

So far, the current registration and stitching process have been fully completed, and the to-be-stitched image B* is saved. If there are other to-be-stitched images, the to-be-stitched image B* is used as the reference image C for a next calculation. The above steps are then repeated to begin the subsequent registration and stitching operation.

As an illustration of the embodiments described above, the following is one example of the panoramic imaging process performed on the human thyroid using a linear array probe, based on the algorithm principles of the present application.

Figure 4:
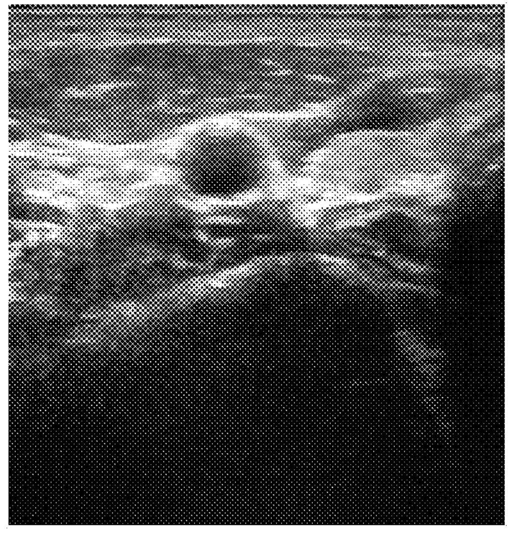
FIG. 4 illustrates a reference image C in one example of scanning the human thyroid gland with a probe.

(1) When scanning the human thyroid with a probe, a first frame scanned is saved as the reference image C, as shown in FIG. 4. FIG. 4 illustrates an image with size x=478 in length and y=500 in width.

Figure 5:
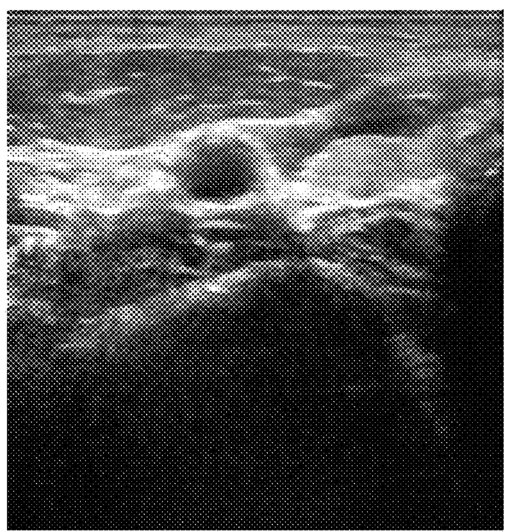
FIG. 5 illustrates a second image scanned as a to-be-stitched image in the example of scanning the human thyroid gland with a probe.

Upon slowly moving the probe to commence scanning, a second image scanned, as depicted in FIG. 5, is saved as image A with x=478 in length and y=500 in width. Due to the software's rapid scan speed, the difference between the two images is not discernible to the naked eye. However, practically, there will exist subtle variations in displacement and variations in pixel of image points that will become apparent from the data during the subsequent registration process, which will not be elaborated upon herein. We are now ready to begin the registration and stitching process.

Figure 6:
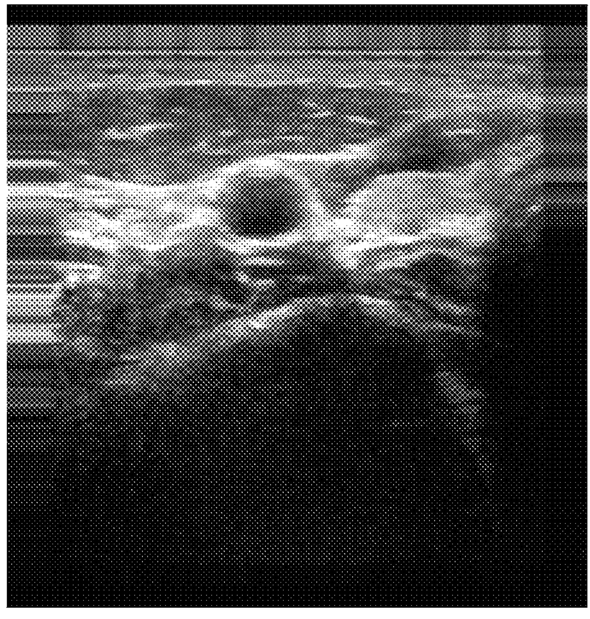
FIG. 6 illustrates the expanded image A* in the example of scanning the human thyroid gland with a probe.
Figure 7:
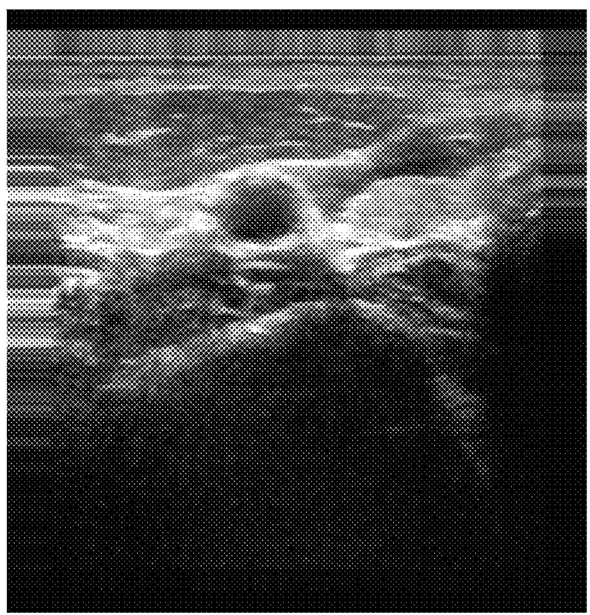
FIG. 7 illustrates the expanded image C* in the example of scanning the human thyroid gland with a probe.

(2) Images A and C are expanded into images A* and C*, respectively, with side length δ of the square area set to 80. Therefore, the expanded A* and C* both have a size of x=558 in length and y=580 in width. The number of the squares can be determined as (int)((x+δ)/δ)*(int)((y+δ)/δ), which rounds to 6*7=42 after integer conversion. The expanded image A* is shown in FIG. 6, and the image C* is shown in FIG. 7.

(3) After obtaining images A* and C*, it is ready to start calculating the offset values for each square area of image A* relative to the image C* with the SAD method. Within each square area, a square-shaped comparison element is set, with its side length being half of δ, i.e., 40. The average offset values in the X-axis direction and the Y-axis direction for the 42 areas in image A* relative to the image C* are calculated with the described algorithm, and the values obtained are shown in Table 1.

TABLE 1

Average Offset Values in the X and Y directions for Each Area

| | | | |
|---|---|---|---|
| $OffsetX_1$ | 0 | $OffsetY_1$ | 0 |
| $OffsetX_2$ | 0 | $OffsetY_2$ | 0 |
| $OffsetX_3$ | 0 | $OffsetY_3$ | 0 |

TABLE 1-continued

Average Offset Values in the X and Y directions for Each Area

| | | | |
|---|---|---|---|
| $OffsetX_4$ | 0 | $OffsetY_4$ | 0 |
| $OffsetX_5$ | 0 | $OffsetY_5$ | 0 |
| $OffsetX_6$ | 1 | $OffsetY_6$ | 0 |
| $OffsetX_7$ | 3 | $OffsetY_7$ | 0 |
| $OffsetX_8$ | 1 | $OffsetY_8$ | 0 |
| $OffsetX_9$ | 1 | $OffsetY_9$ | 1 |
| $OffsetX_{10}$ | 1 | $OffsetY_{10}$ | 0 |
| $OffsetX_{11}$ | 5 | $OffsetY_{11}$ | 0 |
| $OffsetX_{12}$ | 3 | $OffsetY_{12}$ | 0 |
| $OffsetX_{13}$ | 7 | $OffsetY_{13}$ | 1 |
| $OffsetX_{14}$ | 4 | $OffsetY_{14}$ | 2 |
| $OffsetX_{15}$ | 3 | $OffsetY_{15}$ | 1 |
| $OffsetX_{16}$ | 4 | $OffsetY_{16}$ | 2 |
| $OffsetX_{17}$ | 9 | $OffsetY_{17}$ | 3 |
| $OffsetX_{18}$ | 3 | $OffsetY_{18}$ | 0 |
| $OffsetX_{19}$ | 5 | $OffsetY_{19}$ | 0 |
| $OffsetX_{20}$ | 5 | $OffsetY_{20}$ | 1 |
| $OffsetX_{21}$ | 2 | $OffsetY_{21}$ | 1 |
| $OffsetX_{22}$ | 8 | $OffsetY_{22}$ | 1 |
| $OffsetX_{23}$ | 10 | $OffsetY_{23}$ | 3 |
| $OffsetX_{24}$ | 1 | $OffsetY_{24}$ | 1 |
| $OffsetX_{25}$ | 3 | $OffsetY_{25}$ | −1 |
| $OffsetX_{26}$ | −1 | $OffsetY_{26}$ | 11 |
| $OffsetX_{27}$ | 4 | $OffsetY_{27}$ | 4 |
| $OffsetX_{28}$ | 5 | $OffsetY_{28}$ | −13 |
| $OffsetX_{29}$ | 5 | $OffsetY_{29}$ | 19 |
| $OffsetX_{30}$ | −2 | $OffsetY_{30}$ | −15 |
| $OffsetX_{31}$ | 15 | $OffsetY_{31}$ | 10 |
| $OffsetX_{32}$ | 12 | $OffsetY_{32}$ | 10 |
| $OffsetX_{33}$ | 17 | $OffsetY_{33}$ | 5 |
| $OffsetX_{34}$ | 3 | $OffsetY_{34}$ | 0 |
| $OffsetX_{35}$ | 5 | $OffsetY_{35}$ | −1 |
| $OffsetX_{36}$ | 0 | $OffsetY_{36}$ | 0 |
| $OffsetX_{37}$ | 0 | $OffsetY_{37}$ | 0 |
| $OffsetX_{38}$ | 0 | $OffsetY_{38}$ | 0 |
| $OffsetX_{39}$ | 0 | $OffsetY_{39}$ | 0 |
| $OffsetX_{40}$ | 0 | $OffsetY_{40}$ | 0 |
| $OffsetX_{41}$ | 0 | $OffsetY_{41}$ | 0 |
| $OffsetX_{42}$ | 0 | $OffsetY_{42}$ | 0 |

From the calculated data, it can be seen that the two images show differentiation to a certain degree across respective areas. By averaging the offset values for all areas in both the X and Y directions, the average offset of the overall images can be derived, which rounds to be OffsetX=3 and OffsetY=1.

(4) Having acquired X and Y offsets for the center points of each area (i.e., the coordinate mapping values of these center points), the linear interpolation API function provided by OpenCL is called to obtain the coordinate mapping values of all points of the image A relative to the image C.

Figure 8:
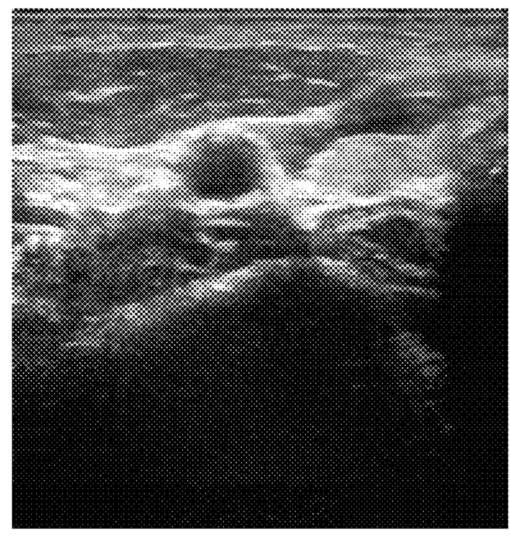
FIG. 8 illustrates the registration image B in the example of scanning the human thyroid gland with a probe.

(5) Subsequently, based on the coordinate mapping values for all these points, deform operation is performed on image A, and the transformed image is denoted as the registered image B, which is illustrated in FIG. 8.

(6) Each pixel of the registered image B is subtracted from that of the image C to obtain a set of differences {Diff[0,0], Diff[0,1] . . . Diff[x,y]}.

Figure 12:
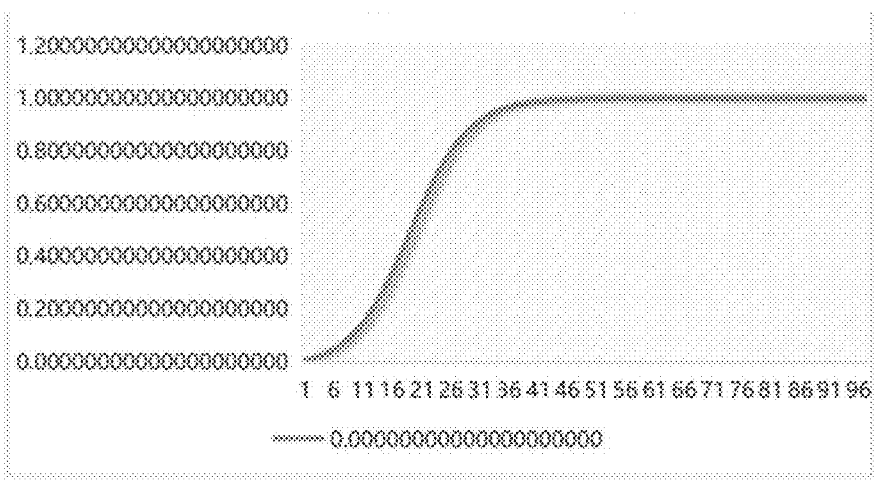
FIG. 12 illustrates a graph showing specific values of arrLUT dataset in the example of scanning the human thyroid gland with a probe.

(7) Next, image correction operation is performed. Take InputValue, where the range of InputValue is 0.01, 0.02, 0.03 . . . 1. Substitute InputValue into the formula OutputValue=InitialValue+(FinalValue−InitialValue)/(1+exp(−Slope*4*(InputValue−Brkpt))). Here, InitialValue represents the initial value of the curve, which in this embodiment equals to 0; FinalValue represents the final value of the curve, which in this embodiment equals to 1; Slope represents the slope of the curve, which in this embodiment equals to 5; Brkpt represents the inflection point value of the curve, which embodiment equals to 0.2. A set of 100 OutputValue values can be obtained, which constitutes the arrLUT dataset. The specific values of the arrLUT Dataset are shown in Table 2 below and FIG. 12.

TABLE 2

| Index of Element in arrLUT Dataset | Value of Element in arrLUT Dataset |
|---|---|
| 1 | 0.00000000000000000000 |
| 2 | 0.00482121755076000000 |
| 3 | 0.01064716854002000000 |
| 4 | 0.01767112042297000000 |
| 5 | 0.02611605771505000000 |
| 6 | 0.03623579427260000000 |
| 7 | 0.04831433387387000000 |
| 8 | 0.06266256926517000000 |
| 9 | 0.07961122185763000000 |
| 10 | 0.0994988 229 670000000 |
| 11 | 0.12265362496639000000 |
| 12 | 0.14936873857737000000 |
| 13 | 0.17987065937838000000 |
| 14 | 0.21428274855731000000 |
| 15 | 0.25258710575478000000 |
| 16 | 0.29459029106190000000 |
| 17 | 0.33989990295652000000 |
| 18 | 0.38791927946121000000 |
| 19 | 0.43786584215251000000 |
| 20 | 0.48881467031134000000 |
| 21 | 0.53976349847017000000 |
| 22 | 0.58971006116147000000 |
| 23 | 0.63772943766617000000 |
| 24 | 0.68303904956078000000 |
| 25 | 0.72504223486790000000 |
| 26 | 0.76334659206537000000 |
| 27 | 0.79775868124431000000 |
| 28 | 0.82826060204531000000 |
| 29 | 0.85497571565629000000 |
| 30 | 0.87813051763598000000 |
| 31 | 0.89801811876505000000 |
| 32 | 0.91496677135751000000 |
| 33 | 0.92931500674882000000 |
| 34 | 0.94139354635008000000 |
| 33 | 0.95151328290763000000 |
| 36 | 0.95995822019971000000 |
| 37 | 0.96698217208266000000 |
| 38 | 0.97280812307192000000 |
| 39 | 0.97762934062269000000 |
| 40 | 0.98161153757530000000 |
| 41 | 0.98489557512917000000 |
| 42 | 0.98760035618976000000 |
| 43 | 0.98982568252605000000 |
| 44 | 0.99165493992235000000 |
| 45 | 0.99315753910003000000 |
| 46 | 0.99439108276687000000 |
| 47 | 0.99540325626176000000 |
| 48 | 0.99623345542961000000 |
| 49 | 0.99691417406995000000 |
| 50 | 0.99747217711666000000 |
| 51 | 0.99792948644503000000 |
| 52 | 0.99830420511686000000 |
| 53 | 0.99861120380257000000 |
| 54 | 0.99886269059917000000 |
| 55 | 0.99906868283269000000 |
| 56 | 0.99923739689024000000 |
| 57 | 0.99937556977860000000 |
| 58 | 0.99948872400190000000 |
| 59 | 0.99958138550590000000 |
| 60 | 0.99965726284150000000 |
| 61 | 0.99971939433898000000 |
| 62 | 0.99977026893131000000 |
| 63 | 0.99981192529546000000 |
| 64 | 0.99984603316984000000 |
| 65 | 0.99987396003026000000 |
| 66 | 0.99989682574583000000 |
| 67 | 0.99991554737197000000 |
| 68 | 0.99993087585358000000 |
| 69 | 0.99994342609513000000 |
| 70 | 0.99995370159326000000 |
| 71 | 0.99996211461338000000 |
| 72 | 0.99996900271477000000 |
| 73 | 0.99997464228432000000 |
| 74 | 0.99997925961966000000 |
| 75 | 0.99998304000516000000 |
| 76 | 0.99998613514384000000 |
| 77 | 0.99998866924301000000 |
| 78 | 0.99999074399729000000 |
| 79 | 0.99999244266870000000 |
| 80 | 0.99999383342742000000 |
| 81 | 0.99999497208717000000 |
| 82 | 0.99999590434481000000 |
| 83 | 0.99999666761408000000 |
| 84 | 0.99999729252695000000 |
| 85 | 0.99999780416291000000 |
| 86 | 0.99999822305538000000 |
| 87 | 0.99999856601578000000 |
| 88 | 0.99999884680818000000 |
| 89 | 0.99999907670167000000 |
| 90 | 0.99999926492262000000 |
| 91 | 0.99999941902495000000 |
| 92 | 0.99999954519330000000 |
| 93 | 0.99999964849123000000 |
| 94 | 0.99999973306444000000 |
| 95 | 0.99999980230714000000 |
| 96 | 0.99999985899827000000 |
| 97 | 0.99999990541305000000 |
| 98 | 0.99999994341426000000 |
| 99 | 0.99999997452702000000 |
| 100 | 1.00000000000000000000 |

Figure 9:
FIG. 9 illustrates the to-be-stitched image B* in the example of scanning the human thyroid gland with a probe.

(8) Substitute into the formula Coeff[i]=arrLUT[Diff*[i]], where i∈[0, x*y), x equals to 478, and y equals to 500, to correct the registration image B and thus obtain the to-be-stitched image B*, as shown in FIG. 9.

Figure 10:
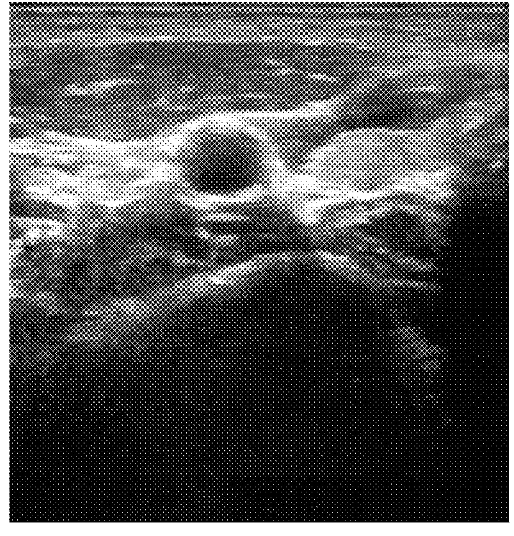
FIG. 10 illustrates a result image after the stitching is completed in the example of scanning the human thyroid gland with a probe.

(9) After the to-be-stitched image B* is obtained, stitching operation is performed, in which based on the previously calculated average offset values OffsetX=3, OffsetY=1, the to-be-stitched image B* is stitched onto image C, and there exists the overlapping part between the two images. The overlap coefficient SpaceCoeffCount is defined as 20, indicating that a first 20 units of width in the overlapping part needs to corrected, while the rest of the overlapping part does not need any operation. The result after the stitching is completed is shown in FIG. 10, with its size of x=481 in length and y=501 in width.

The to-be-stitched image B* serves as the new reference image C to subsequently repeat the above steps for a next panoramic registration and stitching.

Figure 11:
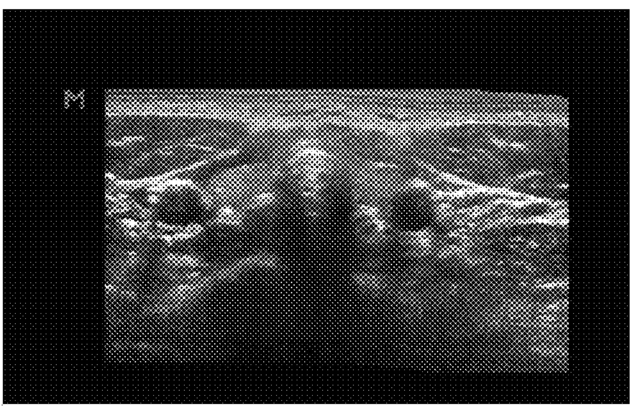
FIG. 11 illustrates a final panoramic resulting image obtained after all the to-be-stitched images are completed.

After completion of all the steps, the final panoramic resulting image is obtained as shown in FIG. 11.

From FIG. 11, it can be seen that FIG. 11 is a panoramic image of the human thyroid gland after stitching. In the panoramic resulting image, the thyroid tissue is clear, and the image is continuous and complete, solving problems such as noise and tissue movement during the probe scanning process, which may adversely affect the image quality, thus contributing to clear ultrasonic panoramic images.

There are many solutions and approaches to carry out the present application, and the above description is merely to illustrate the preferred embodiment of this invention. It should be noted that various variations and modifications can be made for those skilled in the art without departing from the principle of this invention, and those variations and modifications should also be considered within the scope of protection of this invention. In the present embodiment, any components which have not been expressly detailed herein can be realized with existing technology.

What is claimed is:

1. A method for ultrasonic panoramic imaging, comprising:

(1) acquiring one frame from to-be-stitched images, determining whether this frame is a first frame among a plurality of the to-be-stitched images, and directly using it as an initial reference image C if it is the first frame or otherwise proceeding to step (2) if it is not the first frame;

(2) acquiring an image A other than the reference image C, expanding a perimeter of the image A based on values of neighboring pixels thereof to generate an image A*, and expanding a perimeter of the reference image C based on values of neighboring pixels thereof to generate an image C*;

(3) dividing the image A* and the image C* equally into n areas, calculating by a sum of absolute differences (SAD) method an average offset of image A* relative to the image C* in each area, where n is a positive integer;

(4) obtaining average offset values in X and Y directions of image coordinates in image A* relative to the image C* for each of the n areas, adding corresponding average offsets to the coordinates of the center points of each area respectively to acquire a new coordinate of n points for the image A relative to the image C, obtaining average offsets of the overall image by averaging the new coordinates of the n points, and obtaining coordinate mapping values for all points of image A relative to the image C after interpolation is performed on the new coordinates of the n points;

(5) traversing each pixel of the image A based on the obtained coordinate mapping values, performing a mapping thereon according to corresponding coordinates and deforming it into a registered image B;

(6) traversing each pixel of the registered image B and the reference image C by calculating a difference of pixels at corresponding positions to obtain a set of pixel differences; traversing the set of pixel differences by comparing the set with 99 respectively and taking the smaller value to obtain a new set of differences;

(7) obtaining a lookup table based on a calibration curve;

(8) correcting the registered image B to obtain a to-be-stitched image B*; and (9) stitching, by weighted average method for overlapping areas, the to-be-stitched image B* with one previous panoramic resulting image C based on overall average offset, to obtain a composite image D.

2. The method for ultrasonic panoramic imaging according to claim 1, wherein step (3) further comprises:

(3.1) setting a square-shaped comparison unit as a minimum comparison range for each area, and in a first comparison operation, an area where the comparison unit is located in upper left corner of A*1 is denoted as Kernel1, and the area where the comparison unit is located in upper left corner of C*1 is denoted as Kernel2;

(3.2) performing subtraction on each pixel point of Kernel1 and Kernel2 to calculate the difference with the pixel values of corresponding points and obtain differences of a plurality of corresponding pixels, then summing up the differences of all the pixels to obtain the Sum of Absolute Differences (SAD) results for Kernel1 and Kernel2 denoted as Sum1, and saving center coordinate common to Kernel1 and Kernel2 denoted as (x1, y1);

(3.3) moving, in a second comparison, Kernel1 and Kernel2 one step to a right side respectively and continuing to repeat step (3.2) to obtain a second SAD result denoted as Sum2 and coordinate (x2, y2), repeating step (3.2) again to further move Kernel1 and Kernel2 one step to the right side until Kernel1 and Kernel2 move to the upper right corner of A*1 and C*1, then moving one step downward to continue with the SAD calculation until Kernel1 and Kernel2 move across the entire areas of A*1 and C*1, and thus obtaining k2 SAD results including k2 Sum values;

(3.4) identifying a minimum value out of said k2 Sum values and a coordinate value (xmin, ymin) corresponding to the minimum value to serve as a final calculation result for this area, and this coordinate value represents the coordinate of the position with the highest similarity in position within the area of the two images; and (3.5) calculating the average offset value for this area in which coordinate of the center point of the area is subtracted from the coordinate value (xmin, ymin) to obtain the average offsets OffsetX1 and OffsetY1 in X and Y directions.

3. The method for ultrasonic panoramic imaging according to claim 2, wherein step (4) further comprises:

calculating for all the areas the average offset values in X and Y directions {OffsetX1, OffsetX2 . . . OffsetXn}, {OffsetY1, OffsetY2 . . . OffsetYn}; and adding coordinate of the center point of each area in the image A* to corresponding average offsets respectively to obtain new mapping coordinates of n points for the image A relative to the image C, and obtaining average offsets OffsetX, OffsetY of the overall image by averaging the average offset values in the X and Y directions across all the areas.

4. The method for ultrasonic panoramic imaging according to claim 3, further comprising: performing an interpolation operation on the new mapping coordinates of the n points for the image A relative to the image C, to obtain the coordinate mapping values for all the points of the image A relative to the image C.

5. The method for ultrasonic panoramic imaging according to claim 4, wherein step (5) of traversing each pixel of image A, performing the mapping thereon according to the corresponding coordinates and deforming it into the registered image B is performed with a formula given by $$dst[x,y]=src[yMap[x,y],xMap[x,y]],$$

where dst denotes a target image, i.e., the registered image B;

src denotes a source image, i.e., image A; x and y represent x-axis coordinate and y-axis coordinate, respectively; and yMap and xMap represent y-coordinate mapping and x-coordinate mapping from coordinate mapping values of all the points of image A relative to the image C in step (4).

6. The method for ultrasonic panoramic imaging according to claim 5, wherein the calibration curve of step (7) is given by:

$$OutputValue=Initial\ Value+(FinalValue-Initial\ Value)/(1+\exp(-Slope*4*(InputValue-Brkpt))),$$

where InitialValue denotes an initial value of the curve;

Final Value denotes a final value of the curve;

Slope is a slope of the curve;

Brkpt denotes a value of inflection point of the curve;

InputValue denotes input parameter, which is a collection consisting of a plurality of numerical values; and OutputValue denotes a set of output values obtained by substituting the values of, which is referred to as the lookup table and is denoted as the arrLUT dataset.

7. The method for ultrasonic panoramic imaging according to claim 6, wherein step (8) further comprises:

obtaining a set of registration coefficient Coeffx*y in accordance with a formula given by Coeff[i]=arrLUT [Diff*[i]] where i∈[0,x*y), and correcting the registered image B in accordance with a formula given by ImageB[i]=Coeff[i]*ImageB[i]+(1−Coeff[i])*ImageC[i], where i∈[0, x*y), ImageB[i] denotes i-th pixel of the image B, ImageC[i] denotes i-th pixel of image C, resulting in the to-be-stitched image B*.

8. The method for ultrasonic panoramic imaging according to claim 7, wherein the stitching by the weighted average method in step (9) is specified by:

(9.1) stitching the to-be-stitched image B* onto the reference image C based on the overall average offset OffsetX and OffsetY, to obtain the composite image D, wherein there is an overlapping area between the two images in the composite image D which requires further correction and smoothing;

(9.2) setting an overlap coefficient SpaceCoeffCount, indicating that image correction is performed for the area having a width defined by SpaceCoeffCount in the overlapping area, and obtaining a correction dataset arrCoefficient with a number of SpaceCoeffCount in accordance with a formula given by arrCoefficient[i]=((i+1))/SpaceCoeffCount where i∈[0, SpaceCoeffCount);

(9.3) Basing on a formula given by ImageD[x,y]=(1−arrCoefficient[x])*ImageC[x,y]+arrCoefficient[x]*ImageB*[x,y], where [x,y] denotes coordinate of a point in the image, ImageD denotes the composite image D, ImageC denotes the reference image C, and ImageB* denotes the to-be-stitched image B*.

9. A computer device, comprising a memory, a processor, and a computer program stored on the memory and executable on the processor, wherein the processor is configured to execute the computer program to implement the method according to claim 1.

10. A non-transitory computer-readable storage medium storing a computer program thereon, wherein the computer program, when executed by a processor, is configured to implement the method according to claim 1.

* * * * *